(12) United States Patent
Dreier

(10) Patent No.: US 6,213,992 B1
(45) Date of Patent: Apr. 10, 2001

(54) DISPOSABLE GARMENT WITH INSPECTION PORTHOLE

(75) Inventor: Kimberly Ann Dreier, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/931,676

(22) Filed: Sep. 16, 1997

Related U.S. Application Data

(63) Continuation of application No. 08/688,387, filed on Jul. 30, 1996, now abandoned.

(51) Int. Cl.$^7$ ........................................ A61F 13/15
(52) U.S. Cl. ........................ 604/385.1; 604/385.2
(58) Field of Search ................... 604/358–361, 604/385.1, 385.2, 393–395, 389–391; 2/78.2, 234, 403; 128/855, 886; 602/47, 59

(56) References Cited

U.S. PATENT DOCUMENTS

| | | |
|---|---|---|
| 3,759,261 | 9/1973 | Wang . |
| 3,918,454 | 11/1975 | Korodi et al. . |
| 3,952,746 | 4/1976 | Summers . |
| 4,022,211 | 5/1977 | Timmons et al. . |
| 4,892,536 | 1/1990 | DesMarais et al. . |
| 4,944,733 * | 7/1990 | Casale ................................ 2/405 |
| 4,955,876 | 9/1990 | Millner . |
| 4,968,312 | 11/1990 | Khan . |
| 5,062,840 | 11/1991 | Holt et al. . |
| 5,078,708 | 1/1992 | Haque . |
| 5,207,663 * | 5/1993 | McQueen ............................ 604/358 |
| 5,269,775 | 12/1993 | Freeland et al. . |
| 5,304,159 | 4/1994 | Tanji et al. . |
| 5,342,342 | 8/1994 | Kitaoka . |
| 5,344,516 | 9/1994 | Tanji et al. . |
| 5,354,289 | 10/1994 | Mitchell et al. . |
| 5,364,381 | 11/1994 | Soga et al. . |
| 5,417,680 | 5/1995 | Kimura et al. . |
| 5,462,541 | 10/1995 | Bruemmer et al. . |
| 5,569,229 * | 10/1996 | Rodgers ............................ 604/385.1 |

FOREIGN PATENT DOCUMENTS

| | | |
|---|---|---|
| 2033595 | 7/1992 | (CA) . |
| 802243 * | 2/1951 | (DE) ........................................ 2/234 |

* cited by examiner

*Primary Examiner*—John G. Weiss
*Assistant Examiner*—K. M. Reiche
(74) *Attorney, Agent, or Firm*—Thomas J. Osborne, Jr.; David M. Weirich; Steven W. Miller

(57) ABSTRACT

A disposable garment, such as a diaper, having a liner, an absorbent core and a liquid impervious bottom sheet. Coextensive openings are formed in the liner, bottom sheet and core, and a transparent layer of material overlays the openings to form a window through the openings into the diaper. An opaque, pliable cover is preferably attached to an exterior surface of the bottom sheet so as to overlie the transparent window. The cover includes a layer of adhesive material to enable the cover to be releasably affixed to the window. The cover preferably further includes a tab, the tab and adhesive cooperating to enable the cover to be selectively pulled back to allow for viewing through the transparent layer into the diaper, and then replaced over the opening to conceal the contents of the diaper.

18 Claims, 5 Drawing Sheets

DISPOSABLE GARMENT WITH INSPECTION PORTHOLE

This is a continuation of application Ser. No. 08/688,387, filed on Jul. 30, 1996, now abandoned.

TECHNICAL FIELD

The present invention relates to disposable, absorbent garments and, more particularly, to a disposable garment in which an inspection porthole with a flexible cover is provided on the rear portion of the garment to enable a caretaker to selectively and easily determine whether the garment is soiled.

BACKGROUND OF THE INVENTION

Today, disposable, absorbent garments, such as diapers, are widely used in infant and toddler care, and in the care of incontinent adults, as a means of containing, isolating and disposing of bodily wastes. These garments have generally replaced reusable, washable cloth garments as the preferred means for these applications, and the typical disposable garment is a composite structure containing a number of layers of material. Included in these layers of material are a liquid impermeable outer layer or backsheet, one or more layers of woven or non-woven material forming an absorbent core, and a liquid permeable inner layer or liner. The layers comprising the garment are generally secured together by lines of adhesive, with the backsheet and liner usually directly adhesively interconnected around the periphery of the garment. Elastic bands are often provided along the longitudinal sides of the garment to constrict the liner and backsheet to produce leg cuffs which fit snugly about the wearer's legs. In addition, closure devices, such as adhesive tabs, may be provided for removably fitting and holding the sides of the garment together about the waist of the wearer. Alternatively, the garment may be folded and sealed or otherwise attached along opposing side edges to form a pant or brief.

While many advancements have been made in the field of disposable garments for both infants and adults, which have enabled them to be widely preferred over conventional cloth garments, a number of problems still exist. Among the problems experienced with these disposable garments is the inability to determine whether the garment has been soiled without substantially removing the garment. It is desirable to detect soiling of the garment as soon after it occurs as possible, in order to reduce the occurrence of diaper rashes and other skin irritations and infections. Diapers and other disposable garments have traditionally been produced with opaque back or outer sheets to provide a sanitary appearance for the diaper. Unfortunately, however, the opaqueness of the sheets also serves to conceal the presence of waste material in the diaper.

Currently, there are a limited number of options available to a caretaker for determining whether a garment, such as a diaper, has been soiled. The first of these options is to smell the diaper in order to detect the odor of stool or urine. While this option is non-intrusive to the wearer, it is highly subject to error, since the deodorants applied to the diaper may mask the odor of the waste. Another option is for the caretaker to at least partially remove the garment from the wearer to see whether it is soiled. While this method is more accurate, it is also more invasive and inconvenient, requiring at least a partial removal of the wearer's clothing and diaper. A third option for inspecting the diaper is for the caretaker to stick a finger into the rear portion of the diaper to "feel" whether it is soiled.

While this method also tends to be very accurate, it can be a rather inconvenient and/or unpleasant experience for at least the caretaker. Diapers have been developed which include transparent portions for viewing bodily waste in the diaper without the need for removing the diaper. For instance, Haque, U.S. Pat. No. 5,078,708, issued Jan. 7, 1992, discloses a diaper which includes a transparent outer layer and an opaque soft lining material. In the Haque diaper, openings in the form of character shapes are provided in both the front and back portions of the soft material, so that soilage can be readily viewed from outside the diaper. While the Haque diaper eliminates the need to remove the diaper to detect soilage, its transparent outer layer creates an unsanitary, unpleasant appearance, since the soilage is visible to not only the caretaker, but also to anyone else who is in visual contact with the wearer before the diaper is changed.

Accordingly, to overcome the above and other problems, it is desirable to have a disposable, absorbent garment which includes an inspection porthole for determining whether the garment has been soiled without removing the garment. Further, it is desirable to have such a garment in which the inspection porthole is concealed when not in use in order to preserve the sanitary outer appearance of the garment.

SUMMARY OF THE INVENTION

Accordingly, it is a principal object of the present invention to provide a disposable absorbent garment for infants and adults which includes an inspection porthole for inspecting the contents of the garment.

In particular, it is a principal object of the present invention to provide a disposable, absorbent garment having a transparent inspection porthole which includes a releasably affixed cover for concealing the inspection porthole when it is not in use.

Another object of the present invention is to provide a disposable garment having a transparent inspection porthole and an at least partially detachable cover in which the cover is pliable so as not to detract from the wearer's comfort.

A further object of the present invention is to provide a disposable garment having an inspection porthole and cover, wherein the cover is reclosable to allow for multiple inspections of the same garment.

Yet another object of the present invention is to provide a garment with the above named advantages which is easy and inexpensive to construct.

A still further object of the present invention is to provide a garment with the above-described features which can be worn as either a diaper, a child training pant or an adult incontinence brief.

Additional objects, advantages and other novel features of the invention will be set forth in part in the description that follows and, in part, will become apparent to those skilled in the art upon examination of the invention. The objects and advantages of the invention may be realized and obtained by means of the instrumentalities and combinations particularly pointed out in the appended claims.

To achieve the foregoing and other objects, and in accordance with the purposes of the present invention as described above, a disposable garment is provided comprising a liner, an absorbent core and a liquid impervious backsheet attached to the core. An opening is formed through the liner, core and backsheet to form a passageway between the inner and outer portions of the garment. A transparent layer of material extends over the passageway to form a window into the interior of the garment. An opaque, pliable cover is attached to the backsheet so as to extend over the transparent window. A layer of adhesive material extends about the periphery of the cover, to enable the cover to be releasably affixed to the window. The cover further includes a tab which cooperates with the adhesive material to enable the cover to be selectively pulled back from the transparent window to allow for viewing through the window into the garment. The tab also assists in replacing the cover over the opening to conceal the contents of the diaper.

Still other objects of the present invention will become apparent to those skilled in this art from the following description wherein there is shown and described a preferred embodiment of this invention, simply by way of illustration, of one of the best modes contemplated for carrying out the invention. As will be realized, the invention is capable of other different, obvious aspects all without departing from the invention.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE PREFERRED EMBODIMENTS

Figure 1:
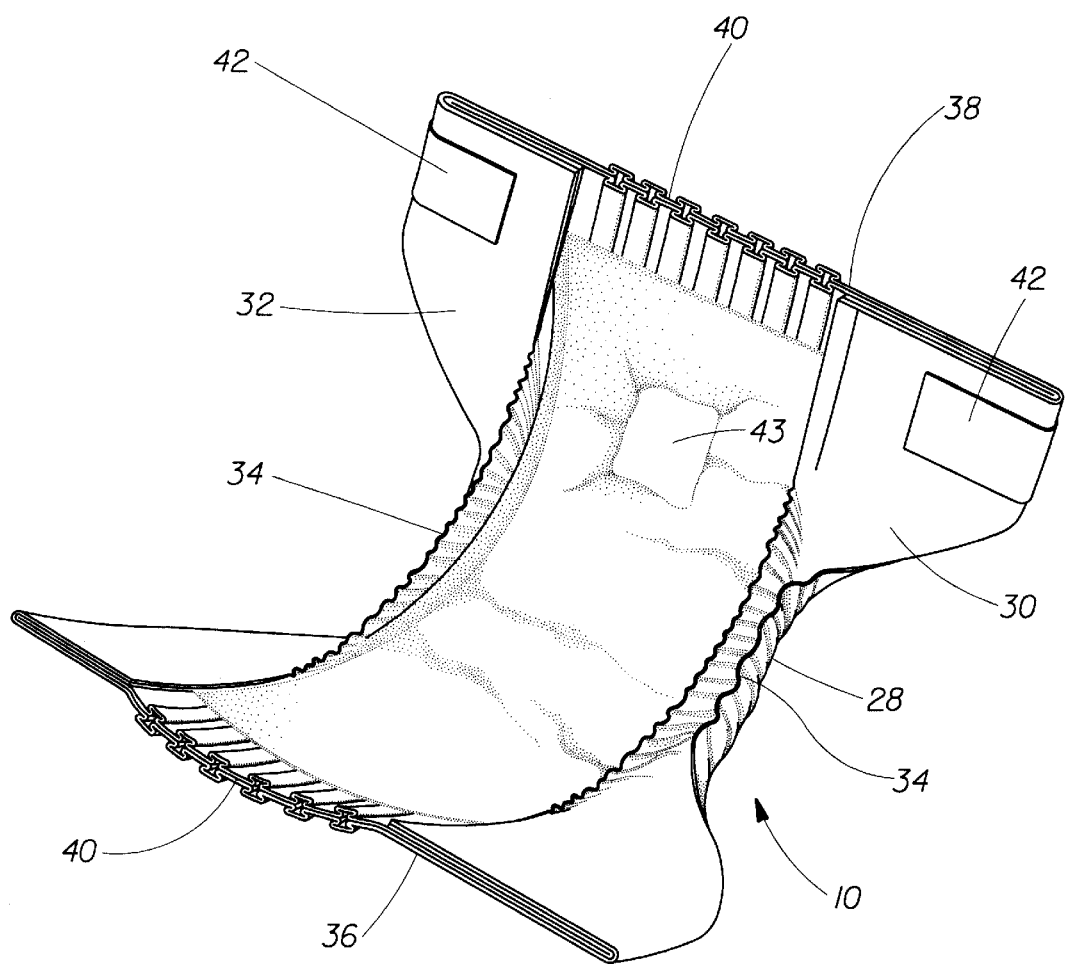
FIG. 1 is a front top perspective view of a garment made in accordance with the present invention, wherein the garment is a diaper.

Referring now to the drawings in detail, FIGS. 1–4 depict a representative embodiment of a garment made in accordance with the present invention, wherein the garment is an infant diaper. The invention will be described with respect to its application on a diaper, however, it is to be understood that the invention is applicable to other disposable, absorbent garments, such as an incontinence brief, without departing from the scope of the invention.

In the representative embodiment shown in the figures, the diaper, designated generally as 10, includes an outer sheet or backsheet 12 extending along the bottom surface of the diaper 10. The backsheet 12 is preferably comprised of a material that is substantially impervious to liquid, such as vinyl plastic or the like, to prevent liquid from leaking through the bottom surface of the diaper. The backsheet 12 has an outer surface 14 which faces away from the wearer and an inner surface 16 which contacts an absorbent core 18 in the diaper 10. The backsheet 12 is preferably opaque, or otherwise made non-transparent to the interior or core of the diaper 10, to present a sanitary and pleasant appearance.

As mentioned above, an absorbent core 18 is preferably positioned adjacent the interior surface 16 of the backsheet 12. Core 18 is preferably rectangular in shape and extends longitudinally, substantially front to back, through the center of the diaper. Preferably, the core 18 is longitudinally shorter than the backsheet 12 to provide a free margin at each transverse edge of the diaper. Core 18 is comprised of one or more layers of woven or non-woven material capable of absorbing and retaining volumes of liquid. The core 18 may be integrally affixed to the backsheet 12, may be peripherally affixed to the backsheet, or not affixed to the backsheet. If affixing is desired, the attachment can be made using any suitable urine stable adhesive or other known bonding means.

Figure 2:
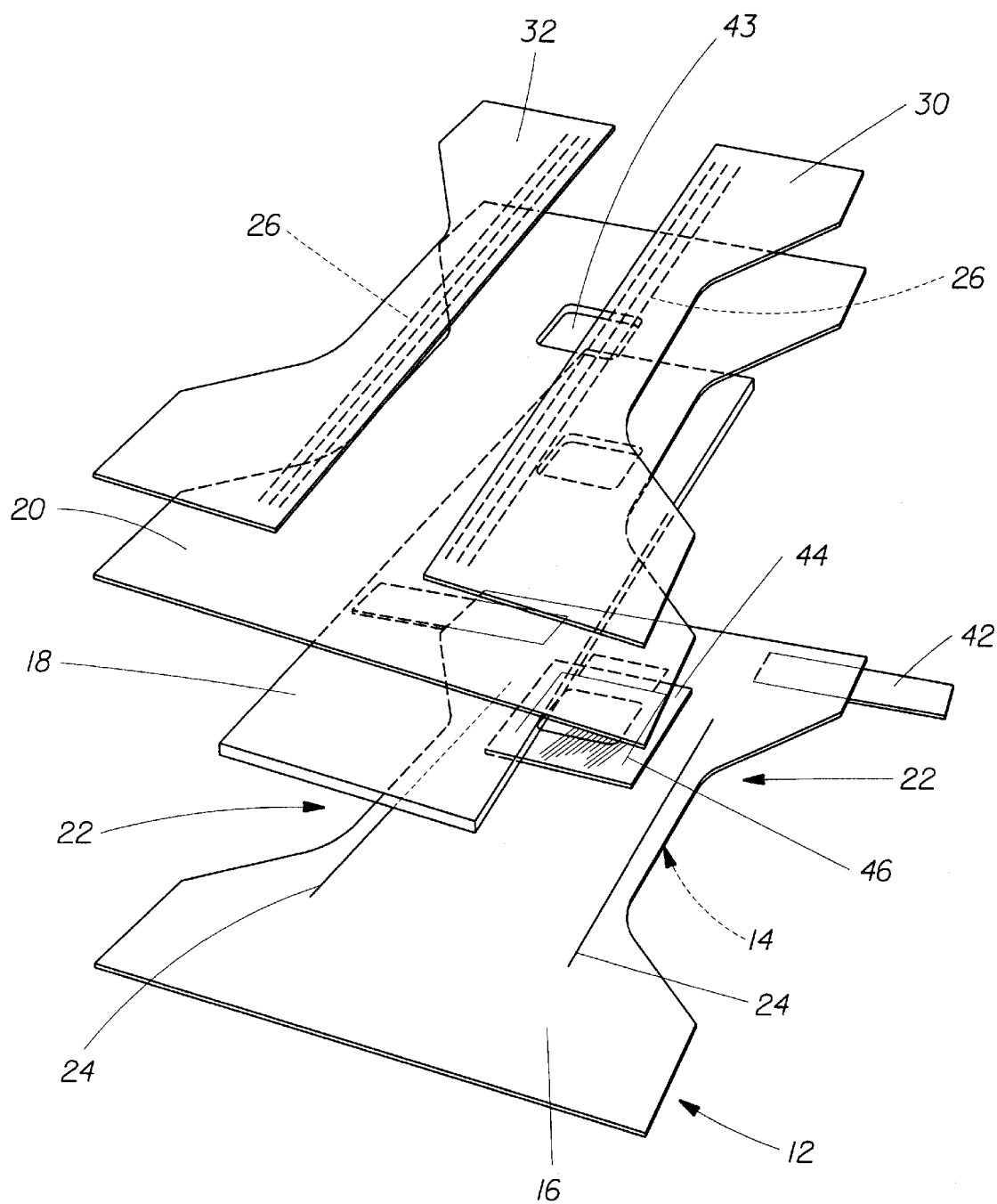
FIG. 2 is a partially exploded view of the garment of FIG. 1.
Figure 3:
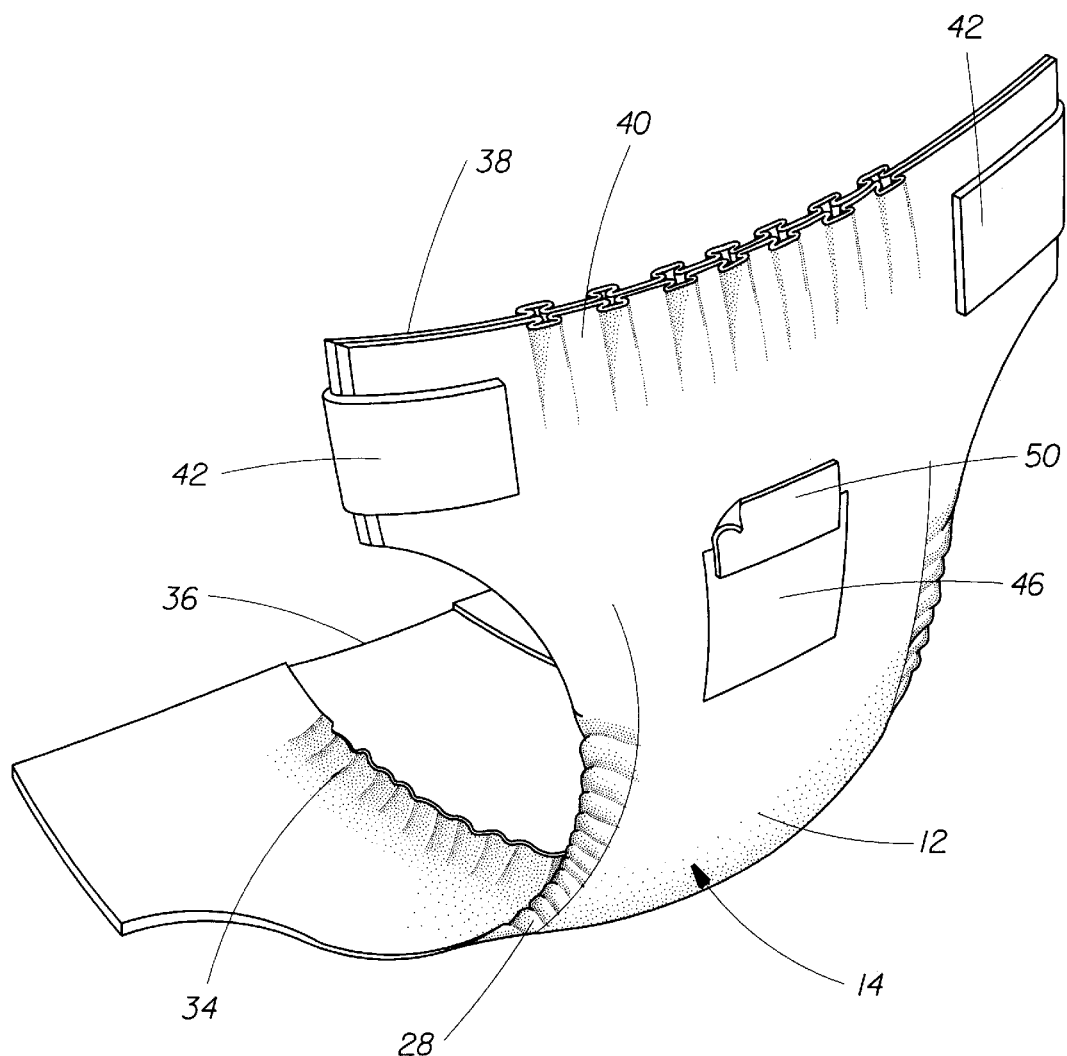
FIG. 3 is a back bottom perspective view of the garment of FIG. 1, depicting the inspection porthole in a first, covered position.

In addition to the backsheet 12 and core 18, the diaper 10 also includes a non-absorbent, liquid permeable, generally inelastic liner 20. Liner 20 extends along the upper surface of the diaper 10 in contact with the wearer's skin. As shown in FIG. 2, the liner 20 may generally correspond in size and shape to the backsheet 12. The liner 20 is at least partially, and preferably fully, peripherally affixed to the backsheet 12, laminating the core 18 intermediate the liner and backsheet. The liner 20 may be affixed to the backsheet 12 using any well known method such as adhesives, thermal sealing or ultrasonic welding. The liner 20 is considered to be affixed to the backsheet 12 if the liner is directly attached to the backsheet or indirectly attached to the backsheet through a separate component. The liner 20 is preferably soft, comfortable and non-irritating to the wearer's skin.

As shown in FIG. 2, the backsheet 12 and liner 20 are preferably notched along their longitudinal sides to form cutouts 22. Cutouts 22 form an opening for the wearer's legs when the diaper 10 is folded and attached about the wearer's torso. Attached to the backsheet 12 in a preferred embodiment, along the longitudinal sides of the diaper adjacent the cutouts 22, are contracting structures, such as elastic strips 24. The elastic strips 24 are preferably attached so as to extend substantially parallel to the length of the cutouts 22, and are preferably attached to the backsheet 12 in a pre-strained condition, so that when permitted to relax, the strips tend to gather the backsheet adjacent the cutouts 22 to form outer barrier leg cuffs 28, such as shown in FIG. 1. In addition to the strips 24 on the backsheet 12, a second set of elastic strips 26 are attached to panels 30, 32. Panels 30, 32 are attached to the upper surface of the liner 20 along opposing longitudinal sides of the diaper 10. The elastic strips 26 are similarly attached in a pre-strained condition, so that when permitted to relax, the elastic strips gather the edges of the panels 30, 32 to form inner barrier leg cuffs 34. The inner and outer barrier leg cuffs 28, 34 enable the diaper 10 to fit snugly and comfortably about the wearer's legs, and also minimize the leakage of fluid around the leg openings in the diaper 10. Gathering structures, such as elastomeric material 40, are preferably provided at the front and rear transverse edges 36, 38 of the diaper 10, as shown in FIG. 1, in order to contract the waist portion of the diaper 10 to likewise form a comfortable but snug fit about the wearer's torso.

Closure devices are preferably provided on the diaper 10 for securing the diaper about the wearer's torso. In the representative embodiment shown in the figures, these closure devices comprise adhesive tabs 42 which are secured on opposing sides of the backsheet 12, and which extend around the side edges of the backsheet 12, so that the adhesive surface of the tabs is attached to the rear portion of panels 30, 32 prior to use. To secure the diaper 10 about the wearer, the tabs 42 are peeled away from panels 30, 32 and adhered to the front edges of the backsheet 12 in a conventional manner. While the invention is depicted and described in terms of adhesive tabs as the closure devices, it is to be understood that other closure devices, such as hook loop fasteners and adjustable snaps, or another similar releasable, reclosable device could be used without departing from the scope of the invention. In an alternative embodiment, opposing sides of the garment may be lap or butt welded along their edges to form a pant. Welding the side seams together enables the garment to be used in a pull-on type capacity, such as, for example, in a child's training pant.

As shown in FIGS. 1 and 2, in the diaper 10 of the present invention, a viewing area is provided to enable waste materials to be viewed from outside the diaper. In the representative embodiment shown in the figures, this viewing area comprises an opening 43 which is formed through the backsheet 12, core 18 and liner 20. The opening 43 is preferably located in the rear half of the diaper 10, with the position of the opening 43 being selected so as to coincide with the portion of the diaper 10 where waste materials are most commonly deposited. The opening 43 through the liner 20, core 18 and backsheet 12 forms a passageway between the inner and outer portions of the diaper 10 to form an inspection port 45. In a representative embodiment, the inspection port 45 is substantially rectangular, and is approximately 1 inch by 1.5 inches in area. However, it is to be understood that the size and shape of the opening 43 and inspection port 45 may vary depending upon the type and intended use of the garment, without departing from the scope of the invention. Further, the present invention could be constructed such that an opening is formed through only the core and liner, but not through the back sheet. In this embodiment, the opening through the core and liner would enable soilage in the diaper to be partially visible through the backsheet.

In the representative embodiment shown in FIGS. 1–4, a liquid impermeable overlay 44 is positioned across the opening 43, in order to seal the opening and prevent body fluids and other waste materials from leaking through the inspection port 45. The overlay 44 is preferably comprised of a transparent plastic material, or another similar transparent, liquid impermeable material, so that the interior of the diaper is visible through the overlay 44. In the representative embodiment shown in the figures, the overlay 44 is positioned between the bottom surface of the core 18 and the upper surface 16 of the backsheet 12. In this position, the overlay 44 is sealed to the top surface of the backsheet 12 by any suitable means, such as thermal welding or adhesives, so that a fluid-tight seal is formed between the backsheet and overlay to prevent fluid leakage. While the overlay 44 has been described as being attached between the core 18 and backsheet 12, it is to be understood that the overlay could also be attached on the outer surface 14 of the backsheet 12 without departing from the scope of the invention.

In order to hide the opening 43, overlay 44, and inspection port 45 between inspection viewings of the diaper contents, a concealing structure is provided on the outer surface 14 of the backsheet 12. In the embodiment shown in the figures, the concealing structure is a releasable, reclosable cover 46 which extends across the overlay 44. By "releasable", it is meant that at least a part of cover 46 can be selectively peeled back or disconnected from diaper 10 to reveal inspection port 45 for viewing the interior of the garment in a non-intrusive and convenient manner. The cover 46 is shown in a closed, attached position against the backsheet 12 of the diaper 10 in FIG. 3, and in an open, detached position in FIG. 4. The cover 46 is securely attached (e.g. in a hingeable fashion) along one portion to the outer surface 14 of the backsheet 12 to prevent the cover 46 from separating from the diaper 10. An adhesive material 48 is preferably provided on the side of the cover 46 facing the backsheet 12 to enable the cover to adhere to the overlay 44, or the surface of the backsheet 12 surrounding the overlay. Preferably, the adhesive material applied to the cover 46 remains sticky after detachment to enable the cover to be detached and reattached to the overlay 44 multiple times as needed.

Figure 4:
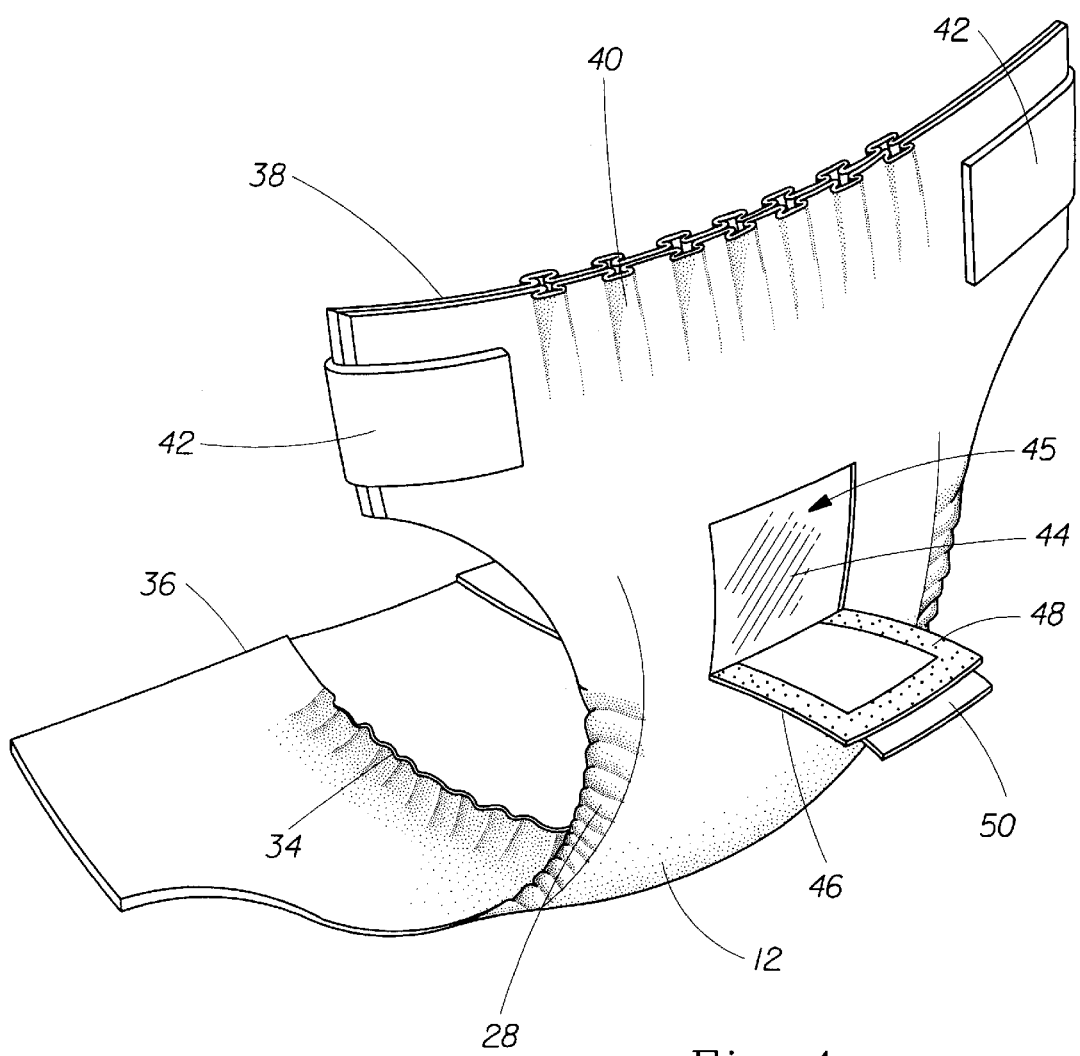
FIG. 4 is a back bottom perspective view of the garment of FIG. 1. depicting the inspection porthole in a second, open or inspection position.

In a preferred embodiment, the cover 46 is rectangular, and the adhesive 48 is applied around the peripheral edges of the cover, as shown in FIG. 4, to enable the cover to be more easily detached from the overlay 44. The cover 46 is preferably comprised of a pliable, non-transparent material, such as a flexible plastic. The cover 46 is preferably pliable to allow the cover to easily conform to shifts in the position of the diaper as the wearer moves, and to prevent the cover 46 from inadvertently poking the wearer and causing discomfort. The cover 46 may be integrally formed with the outer sheet 12 by cutting the outer sheet along three edges and peeling the cut portion back to form the cover. Alternatively, the cover 46 may be a separate piece of material, having the same or different characteristics from the backsheet 12, which is thermal welded or attached by some other permanent means, along one edge to the backsheet 12.

To assist in detaching the cover 46 from the backsheet 12, a detaching mechanism, such as a tab 50, is provided on the cover. The tab 50 extends from at least one edge of the cover 46, beyond the adhesive 48, to provide a loose portion which can be easily grasped to lift the cover away from the overlay.

Figure 5:
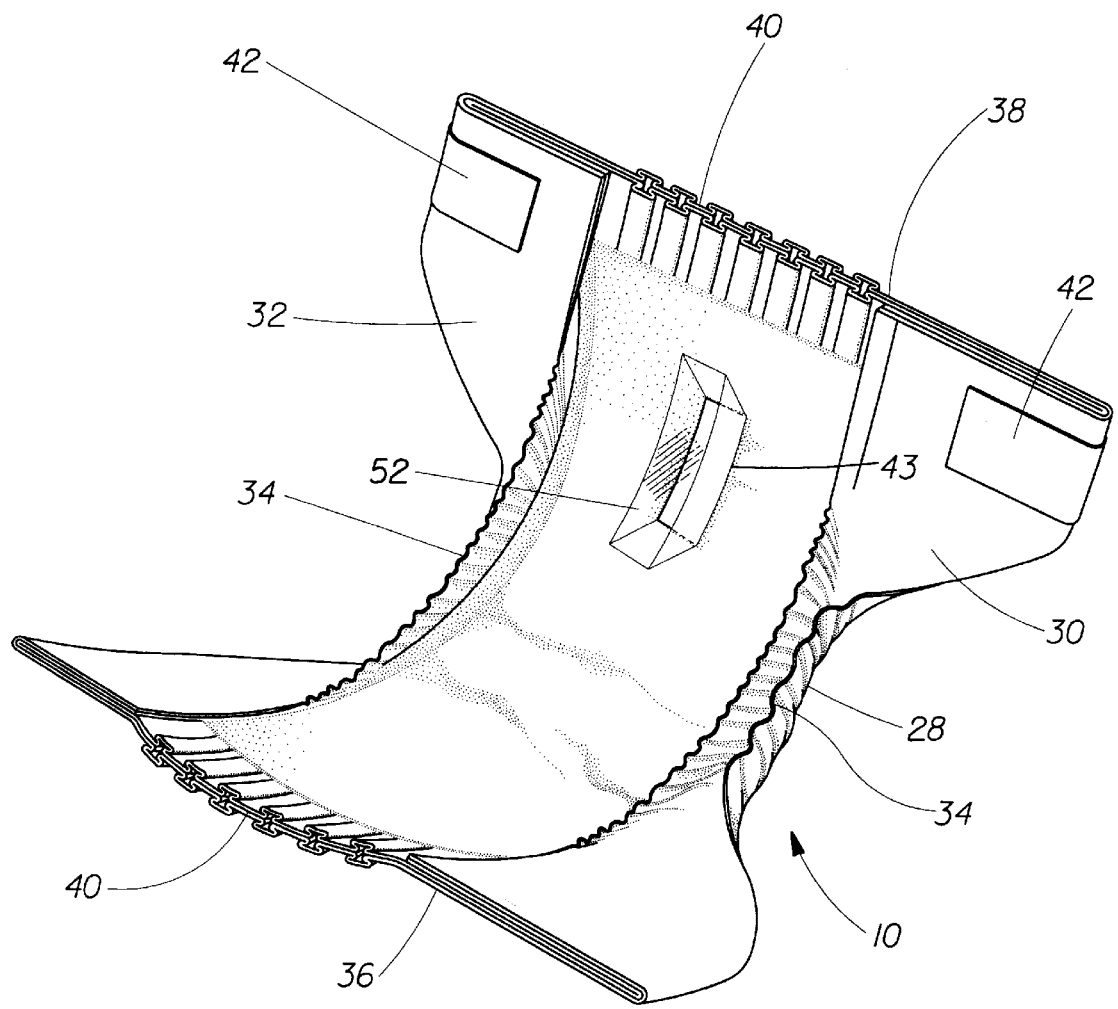
FIG. 5 is a front top perspective view of an alternative embodiment of the garment of the present invention.

While the invention has been described with respect to an opening through the core for viewing waste materials, it is to be understood that it is also possible to construct the present invention by utilizing an absorbent core having a low density such that waste materials are visible through the core, or by using a core in which the density is reduced in the viewing area, to enable the presence of waste materials to be detected through the core. In addition, in an alternative embodiment such as shown in FIG. 5, the inspection port 45 could include structure 52, such as, for example, fiber optic materials, to enable inspection of the inside of the diaper from outside the backsheet.

The foregoing description of preferred embodiments of the invention has been presented for purposes of illustration and description. It is not intended to be exhaustive or to limit the invention to the precise form disclosed. Obvious modifications or variations are possible in light of the above teachings. The embodiment shown and described was chosen in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A disposable garment comprising:
    an absorbent core;
    a liquid impervious outer sheet having an outer surface and an inner surface overlying the core, wherein the core and the outer sheet include an inspection port extending therethrough;
    a liquid impermeable, transparent overlay having an inner overlay surface and an outer overlay surface, wherein the overlay is disposed between the outer sheet and the absorbent core so as to extend across the inspection port to prevent bodily waste materials from leaking through the inspection port in the outer sheet, the transparent overlay being sealingly attached to the outer sheet;

an opaque concealing structure positioned exterior to the outer overlay surface, wherein the concealing structure has a concealing position in which the concealing structure extends over the inspection port; and an adhesive material disposed on the concealing structure for releasably maintaining the concealing structure in its concealing position.

2. A disposable garment as recited in claim 1 wherein the garment includes a liner having an opening which is substantially aligned with the core and outer sheet inspection port.

3. A disposable garment as recited in claim 1 wherein the concealing structure is pliable.

4. A disposable garment as recited in claim 1 wherein the concealing structure is attached to the outer sheet.

5. A disposable garment as recited in claim 1 further comprising a mechanism for releasing the concealing structure from its concealing position over the inspection port.

6. A disposable garment as recited in claim 5 wherein the releasing mechanism comprises a tab.

7. A disposable garment as recited in claim 1 wherein the concealing structure is releasably attachable to the transparent overlay.

8. A disposable garment as recited in claim 1 wherein the concealing structure is hingeably attached to the outer sheet for selective opening and closing.

9. A disposable garment as recited in claim 1 wherein the concealing structure is substantially rectangular.

10. A disposable diaper comprising:

an absorbent core;

an inner liner extending along an inner surface of the core;

a liquid impervious outer sheet extending along an outer surface of the core, the liner, core and outer sheet having an opening extending therethrough;

a liquid impermeable, transparent overlay sealingly attached to an interior surface of the outer sheet and extending across the opening; and a pliable, opaque cover secured to the outer sheet on a side opposite the transparent overlay, the cover including an adhesive material for releasably attaching the cover in a concealing position over the transparent overlay.

11. A disposable diaper as recited in claim 10 wherein the cover is releasably attachable to the transparent overlay.

12. A disposable diaper as recited in claim 11 wherein the cover includes a tab for releasing the cover from the transparent overlay.

13. A disposable diaper as recited in claim 12 wherein the cover is substantially rectangular and a first side of the rectangle is secured to the outer sheet and the opposing side of the rectangle is connected to the tab.

14. A disposable diaper as recited in claim 11 wherein the cover is hingeably attached to the outer sheet for selective opening and closing.

15. A disposable diaper as recited in claim 14 wherein the cover is:

monolithically formed from the outer sheet.

16. The disposable diaper as recited in claim 15 further comprising a mechanism for releasing the cover from its concealing position over the opening.

17. The disposable diaper as recited in claim 16 wherein the releasing mechanism comprises a tab.

18. The disposable diaper as recited in claim 17 wherein the cover is substantially rectangular and a first side of the rectangle is secured to the outer sheet and an opposing side of the rectangle is connected to the tab.

* * * * *